US00PP29167P2

(12) United States Plant Patent
Zlesak

(10) Patent No.: US PP29,167 P2
(45) Date of Patent: Apr. 3, 2018

(54) POLYANTHA ROSE PLANT NAMED 'PHYLLIS SHERMAN'

(50) Latin Name: *Rosa hybrida*
Varietal Denomination: Phyllis Sherman

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 15/530,354

(22) Filed: Jan. 3, 2017

(51) Int. Cl.
*A01H 5/02* (2018.01)

(52) U.S. Cl.
USPC ..... Plt./149
CPC ..... *A01H 5/0222* (2013.01)

(58) Field of Classification Search
USPC ..... Plt./149, 148
CPC ..... A01H 5/022
See application file for complete search history.

*Primary Examiner* — Kent L Bell

(57) ABSTRACT

Polyantha rose plant having a slightly spreading, mounded, well-branched, compact plant habit; vigorous growth; double flowers typically borne in clusters of 6 or more; vivid purplish-pink petals; continuous flowering throughout the growing season; resistance to major fungal diseases; reliable crown hardiness in USDA zone 4, and ability to root and grow vigorously from softwood and semi-hardwood cuttings.

3 Drawing Sheets

Latin name of the genus and species of the plant claimed: *Rosa hybrida.*

Variety denomination: 'Phyllis Sherman'.

BACKGROUND OF THE INVENTION

The primary objective of making this cross was to produce a new rose variety having the continuous blooming habit, compact plant size, glossy foliage, and disease resistance of the female parent and the double flowers, richer flower color, and extensive branching of the male parent. The pollination occurred in late spring 2007. Seed from this cross germinated during the winter of 2007/2008 and 'Phyllis Sherman' was identified as a superior seedling and was first asexually propagated during the summer of 2008.

The present invention relates to a new and distinct variety of rose plant of the polyantha commercial class designated 'Phyllis Sherman'. 'Phyllis Sherman' was originated by me by crossing 'BAIpome' (disclosed in U.S. Plant Pat. No. 16,602) and 'Mountain Mignonette' (not patented).

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Slightly spreading, mounded, well-branched, compact plant habit;
2. Vigorous growth;
3. Double flowers typically borne in clusters of 6 or more;
4. Vivid purplish-pink petals;
5. Continuous flowering throughout the growing season;
6. Resistance to major fungal diseases;
7. Reliably crown hardy in USDA zone 4:
8. Ability to root and grow vigorously from softwood and semi-hardwood cuttings.

Asexual reproduction of this new variety by rooting softwood and semi-hardwood cuttings, as performed at St. Paul, Minn., shows that the foregoing and all other characteristics and distinctions come true to form and are established and transmitted through succeeding generations of asexual propagation.

Comparison with Parents

'Phyllis Sherman' has vivid purplish-pink double flowers (20-30 petaloids that look like petals) and a slightly spreading, mounded, compact habit and differs from its female parent, 'BAIpome', in that 'BAIpome' has single light pink to medium pink blooms (5 petals) and a compact plant habit that is more spreading and shorter. 'Phyllis Sherman' differs from its male parent, 'Mountain Mignonette', in that 'Mountain Mignonette' has a medium pink flower color, petals that do not last as long before abscising, a more rounded plant habit, narrower prickles, and foliage that is less glossy. 'Mountain Mignonette' shares the key trait with 'Phyllis Sherman' in that they both have double flowers. 'BAIpome' shares the key traits with 'Phyllis Sherman' in that they both have glossy foliage, similar shaped prickles, relatively long lasting flowers, and a generally spreading plant habit.

Comparison with Similar Variety

The rose variety with the greatest similarity to 'Phyllis Sherman' is 'KORtwente' (marketed under the name Raspberry Vigorosa™; not patented), a rose sold under both the floribunda and shrub commercial classes by nurseries. Both 'Phyllis Sherman' and 'KORtwente' have double vivid purplish-pink blooms, glossy, disease-resistant foliage, and a slightly spreading, mounded, compact, plant habit. 'Phyllis Sherman' has blooms that are smaller, more double, and borne in larger clusters than 'KORtwente'. 'Phyllis Sherman' has displayed greater crown hardiness in USDA zone 4 than 'KORtwente'.

BRIEF DESCRIPTION OF THE DRAWING

The accompanying illustration shows typical specimens of the vegetative growth, flowers, and hips of this new variety in different stages of development, depicted in color as true as it is reasonably possible.

DETAILED BOTANICAL DESCRIPTION

Figure 1:
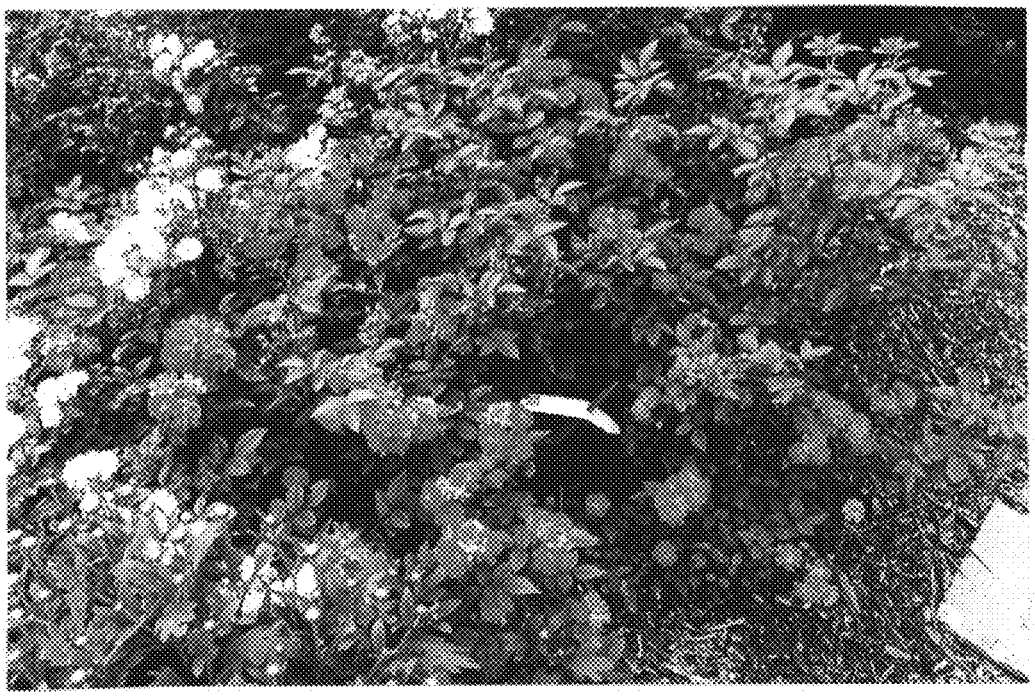
FIG. 1 illustrates a mature plant of 'Phyllis Sherman' flowering in a landscape with white roses of another variety in the background and chrysanthemums in the foreground.
Figure 2:
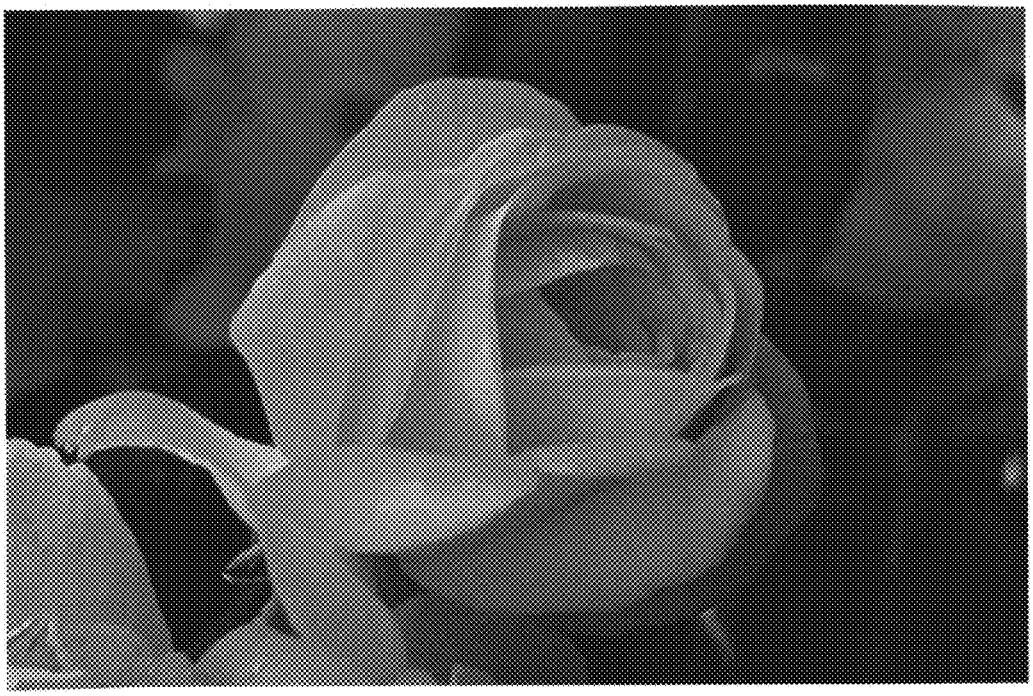
FIG. 2 illustrates an opening flower bud.
Figure 3:
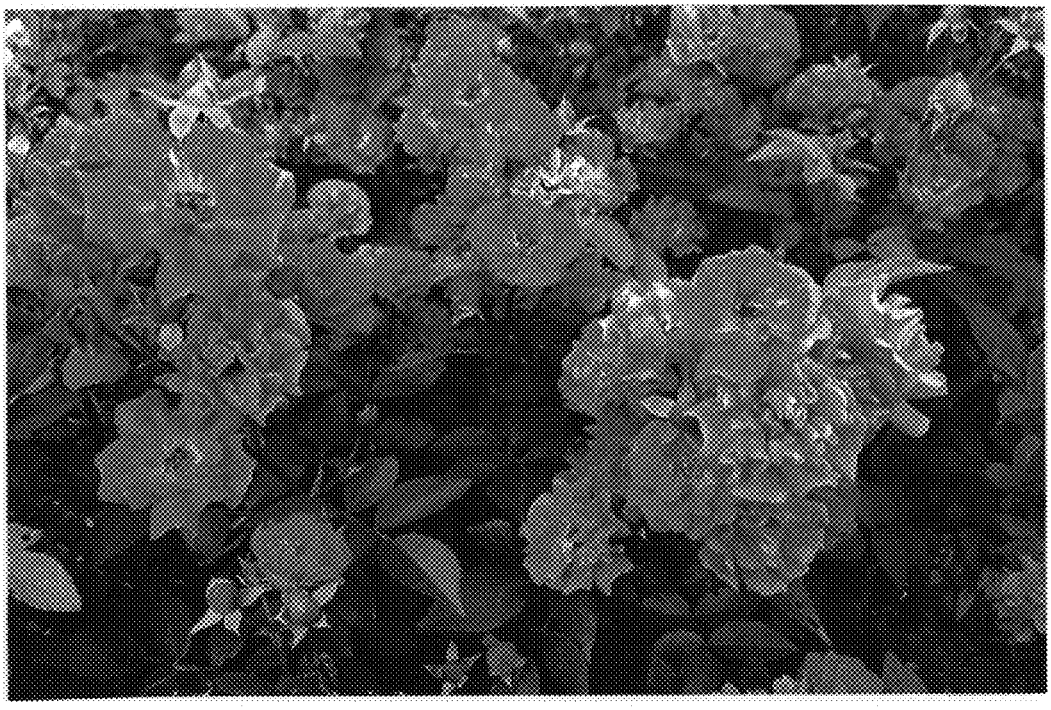
FIG. 3 illustrates a close up view of a group of flowers at different stages of development.
Figure 4:
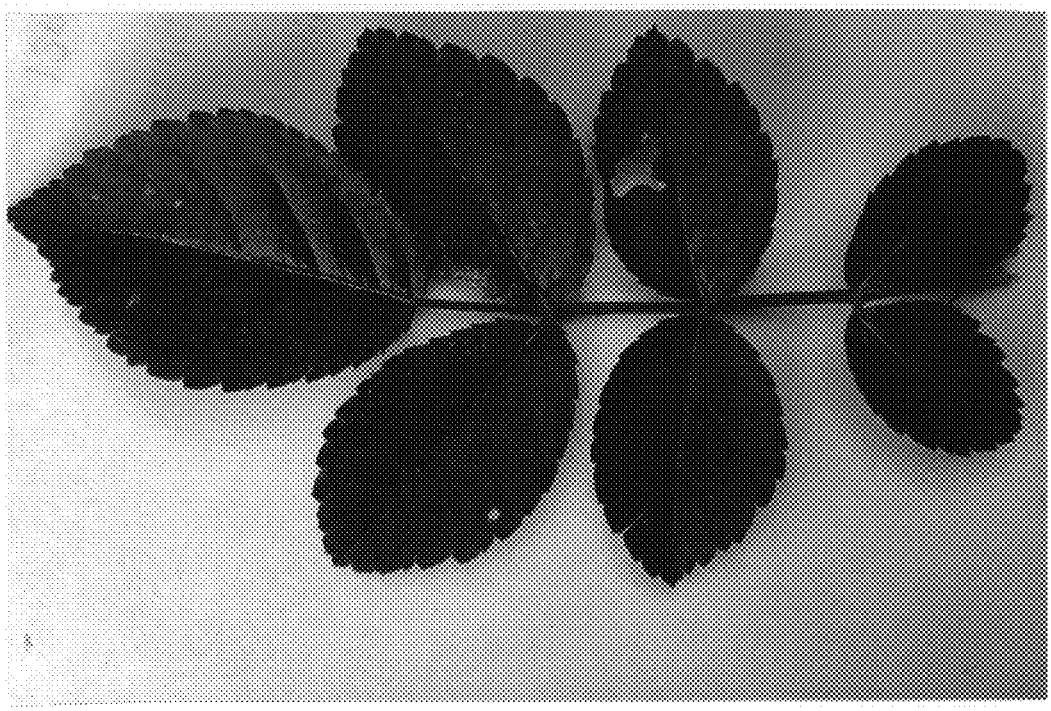
FIG. 4 illustrates a leaf.
Figure 5:
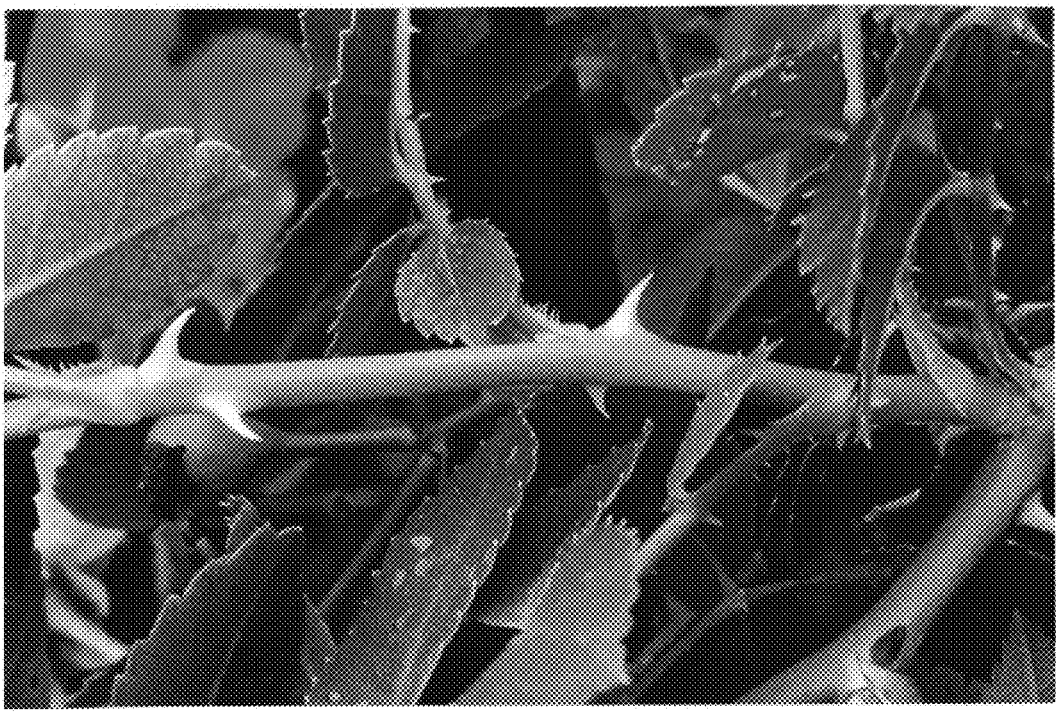
FIG. 5 illustrates stem tissue.
Figure 6:
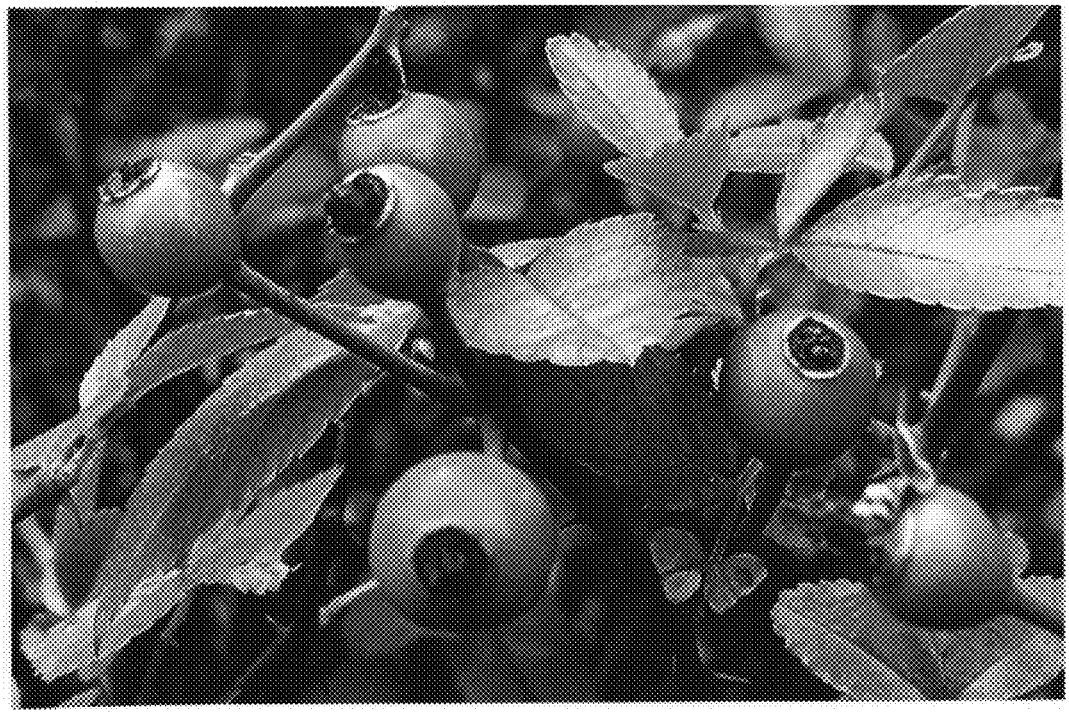
FIG. 6 illustrates ripening hips.

The following is a detailed description of my new rose cultivar with color descriptions using terminology in accordance with The Royal Horticultural Society (London) Colour Chart (2015), except where ordinary dictionary significance of color is indicated. The phenotype of the new cultivar may vary with variations in environmental, climatic, and cultural conditions, as it has not been tested under all possible environmental conditions. Descriptions are based on observations of plants approximately five years of age that were propagated from semi-hardwood cuttings.

Parentage;

*Seed parent.*—'BAIpome' (disclosed in U.S. Plant Pat. No. 16,602).

*Pollen parent.*—'Mountain Mignonette' (not patented).

Classification:

*Botanical.*—*Rosa hybrida.*

*Commercial.*—Polyantha.

Flower:

Blooming habit: Continuous throughout the growing season.

Flower bud:

*Size.*—10-11 mm long and 6-7 mm in diameter when the petals start to unfurl.

*Form.*—The bud form is ovoid and pointed at the distal end.

*Color.*—When sepals first separate, visible petal color is Red-Purple Group 61B at the distal end and transitions to Red-Purple Group 62D at the proximal end. When half blown, the upper or adaxial sides of the petals are a vivid purplish pink and closest to Red-Purple Group N66A. The lower, or abaxial, sides of the petals are Red-Purple Group N57D.

*Sepals.*—Color: Yellow-Green Group 146B on the abaxial side and Yellow-Green Group 145A on the adaxial side. Length: 9-11 mm. Width: 4-5 mm. Shape: ovate to oblong with acuminate tips. Surface texture: Adaxial, Hoary. Abaxial, Generally smooth with some very small glandular hairs. There are three lightly appendaged sepals. There are two unappendaged sepals which have hoary edges.

*Receptacle.*—Color: Yellow-Green Group 146D. Shape: round to slightly elliptic. Size: Small, about 3-4 mm wide and 3-4 mm long. Surface: glabrous.

*Peduncle.*—Length: Medium, averaging about 12-25 mm. Width: Medium, averaging 1.5-2.0 mm. Surface: Generally glabrous with some very small glandulous hairs. Color: Yellow-Green Group 146D. Strength: Stiff, primarily erect.

Bloom:

*Size.*—Medium to large for the polyantha commercial class. Typical open diameter is 30-45 mm.

*Borne.*—Typically clusters of 6-22 blooms are borne at the end of stems in an inflorescence type that can best be described as an elongated or paniculate cyme. The flower at the terminal or distal most end of the inflorescence opens first and then secondary and tertiary flowers open later that have developed on stems originating from axillary buds.

*Form.*—When blooms are in the process of opening: Petals are slightly cupped. As blooms fully open petal edges curl or reflex backward along their vertical axis. This leads to petals that are held relatively straight along their length and that look narrower with age due to the edges that have curled back. The petals at this stage typically produce a bloom with a hemispherical appearance. The hemispherical pattern is formed by petals radiating outward with the petals closest to the sepals generally facing outward to the innermost petaloids facing upward.

*Fragrance.*—Slight. Character of fragrance: Sweet.

*Permanence.*—Blooms retain their hemispherical form to the end.

*Petal and petaloid number.*—Roses have five true petals (except for *Rosa sericea* which typically has four) and all additional petal-like appendages are botanically petaloids. Petaloids are stamens or, in some cases, also pistils that develop into petal-like structures. However, petaloids that do not have obvious remnant stamen development are often called petals in common vernacular in United States Plant Patents and the popular press. 'Phyllis Sherman', like typical roses, has five true petals, between 20-30 petaloids that look like a typical petal, and often 3-5 petaloids that have some visible stamen development typically seen as a single anther along one of the edges of a relatively narrow petal-like structure. The petaloids with anthers attached are found at the transition area in the bloom between the most petal-like petaloids and the stamens. Pistils in 'Phyllis Sherman' do not develop into petaloids. The size and color of the attached anthers on petaloids for 'Phyllis Sherman' varies, but typically is the same as what is described later for anthers. Additionally, the color of the petal-like portion of the petaloid is typical or consistent with the color shared by a true petal or a more petal-like petaloid without visible anther development.

*Petal and petaloid color.*—The adaxial sides of the petals are primarily Red-Purple Group N66A with White Group NN155D at the very base of the petal. The color of the abaxial side of the petals is closest to Red-Purple Group N57D.

*Petal discoloration.*—The general tonality of the adaxial petal distal edge surface of a fully open bloom at the first day through the second day: Red-Purple Group N66A. The general tonality of the adaxial petal surface by day six: Red-Purple Group 67C with up to 25% of the proximal end of the petal being White Group NN155D. The abaxial surface of the petal is Red-Purple Group 73B.

*Petal texture.*—Thick and satiny to the touch.

*Petal length.*—1.4-1.6 cm.

*Petal width.*—0.9-1.3 cm.

*Petal shape.*—Obcordate to obovate.

*Petal margin.*—Entire to slightly undulating.

*Petal apex shape.*—Rounded to obcordate with a small point in the axis.

*Petal base shape.*—Acute to cuneate.

*Petal form.*—Slightly cupped when opening and then petals reflex along the longitudinal axes curling back towards the abaxial surface.

*Arrangement.*—Multiple rows of overlapping petals and petaloids.

*Persistence.*—Petals drop off cleanly before drying.

*Lastingness.*—On the plant: Medium (about 6-8 days). As a cut flower: Medium (about 6 days).

Reproductive organs:

*Stamens.*—Number per flower: 25-40. Anthers — Size: Length before dehiscence: 1.0 mm, Width before dehiscence: 1.0 mm. Length after dehiscence: 0.5 mm. Width after dehiscence: 0.5 mm. Color: Before dehiscense: Yellow Orange Group 17B. After dehiscence: Yellow-Orange Group 22A. Arrangement: Regular and borne around styles. Filaments — Size: Length: Short, 1-4 mm. Width: 0.25 mm. Color: Yellow-Orange Group 17B. Pollen — Color: Yellow Orange Group 17A.

*Pistils.*—Number per flower: 8-15. Stigmas — Color: Yellow-Green Group 150C. Width: 0.5 mm. Styles — Color: Green-Yellow Group 1C. Length: 3-5 mm. Width: 0.3 mm. Ovary — Color of immature ovary: Yellow-Green Group 145D. Shape: elliptic to round. Length: 1 mm.

*Hips.*—The fleshy portion of rose hips is comprised of hypanthium tissue and lining the inside that tissue are achenes — individual indehiscent fruits that typically contain a single embryo within a hard pericarp. Hips are typically abundantly produced on 'Phyllis Sherman'. Sepals abscise upon ripening. Hypanthium: Color when immature: Green Group 146C. Color when mature: Orange-Red Group 30B. Shape: Generally round. Size:10-12 mm long and 10-12 mm wide.

*Achenes (ripe).*—Color: Yellow Green Group 150D. Shape: Irregular. Size: 4-6 mm. Typically there are 6-8 achenes per hip.

Plant:

*Form.*—Spreading and slightly mounded.

*Growth.*—Very vigorous, well-branched, and dense.

*Typical age mature size.*—3 years.

*Mature plant.*—Height about 50 cm and width about 80 cm.

Leaf:

*Form.*—Leaves typically have five to seven leaflets.

*Arrangement.*—Leaves are alternately arranged on stems.

*Size.*—Medium (7-9 cm long and 4-6 cm wide).

*Quantity.*—Normal.

*Leaflet color.*—New foliage: Adaxial side: Yellow-Green Group 146B. Abaxial side: Yellow Green Group 146C. Mature foliage: Adaxial side: Green Group 137A. Abaxial side: Yellow-Green Group 146B.

*Leaflet veination pattern.*—Pinnate reticulate.

*Leaflet veination color.*—The color of the veins is comparable to that of the overall leaf blade. New foliage: Adaxial side: Yellow-Green Group 146B. Abaxial side: Yellow Green Group 146C. Mature foliage: Adaxial side: Green Group 137A. Abaxial side: Yellow-Green Group 146B.

*Leaflet size.*—Terminal leaflets: Medium (3.5-4.0 cm long and 2.0-2.5 cm wide). Non-terminal leaflets: Medium (2.5-3.0 cm long and 1.5-2.0 cm wide).

*Leaflet shape.*—Elliptic.

*Leaflet base shape.*—Rounded.

*Leaflet apex shape.*—Typically acute and in some instances slightly acuminate.

*Leaflet texture.*—Glossy, rugose. On the adaxial side of leaflets the veins are slightly recessed and on the abaxial side they are slightly elevated relative to the general leaf blade.

*Leaflet edge.*—Serrated.

*Petiole and rachis.*—Color. — Adaxial side: Green Group 137B. Abaxial side: Yellow-Green Group 144A.

*Petiole and rachis shape.*—Sulcate.

*Petiole underside.*—Generally smooth with periodic small prickles that are about 0.5 mm long and 0.2 mm wide and Yellow-Green Group 144A in color. Prickles are straight to slightly downward facing.

*Stipules.*—Short (about 0.8-1.0 cm in length and 0.1-0.3 cm in width). Color: Yellow-Green Group 146A, edges with a moderate amount of relatively narrow and small appendages (0.3-1.0 mm long and 0.1 mm wide).

*Disease resistance.*—Resistant to powdery mildew, black spot, and rust under normal growing conditions.

*Pest persistence.*—Not observed.

Stems:

*Strength.*—Strong.

*Length.*—Typically about 20-35 cm.

*Diameter.*—Varies and is most commonly 3-6 mm. Larger stems arising from the base of the plant are about 6-8 mm in diameter, while smaller stems arising from either the base of the plant or side branches arising within the plant canopy are commonly 3-4 mm in diameter.

*Color.*—New stems: Generally Yellow-Green Group 146C. Bark: Smooth. Mature stems: Yellow-Green Group 146B. Bark: Smooth.

Stem prickles:

*Quantity.*—Moderate: typically 2-3 for each internode region.

*Form.*—Straight to very slightly downward hooked.

*Length.*—6-8 mm.

*Width.*—3-6 mm near stem and narrowing to tip.

*Color when young.*—Greyed-Green Group 193B often with some overlaid red color in the sun of Greyed-Red Group 181D.

*Color when mature.*—Between Greyed-Orange Group 174A and Greyed-Orange Group 174B.

*Secondary stem prickles.*—None.

Growth and propagation:

*Propagation.*—Softwood and semi-hardwood stem cuttings have been effective.

*Time required for root initiation and initial development.*—It takes about 2 to 3 weeks during the summer using intermittent mist in the greenhouse without supplemental lighting for cuttings to generate roots.

*Time required to obtain a well-rooted cutting.*—It takes about 6 weeks to produce a well-rooted cutting in a 2 inch pot or cell.

Cytology:

*Ploidy.*—Diploid (2n=2x=14). Meristematic root tip cells in the stage of metaphase of mitosis were observed to have 14 chromosomes under a light microscope at 400× magnification.

Winter hardiness: Consistently crown hardy to United States Department of Agriculture cold hardiness zone 4.

I claim:

1. A new and distinct variety of rose plant of the polyantha class, substantially as herein shown and described, characterized particularly by its slightly spreading, mounded, well-branched, compact plant habit; vigorous growth; double flowers typically borne in clusters of 6 or more; vivid purplish-pink petals; continuous flowering throughout the growing season; resistance to major fungal diseases; reliable crown hardiness in USDA zone 4, and ability to root and grow vigorously from softwood and semi-hardwood cuttings.

* * * * *